United States Patent [19]
Maruyama et al.

[11] Patent Number: 5,948,800
[45] Date of Patent: Sep. 7, 1999

[54] PREVENTIVE OR THERAPEUTIC DRUG FOR ALZHEIMER'S DISEASE

[75] Inventors: Ikuro Maruyama; Kazuhiro Abeyama, both of Kagoshima; Hiroyuki Masayasu, Tokyo, all of Japan

[73] Assignee: A. Nattermann & Cie. GmbH, Cologne, Germany

[21] Appl. No.: 08/905,530

[22] Filed: Aug. 4, 1997

[30] Foreign Application Priority Data

Aug. 27, 1996 [JP] Japan .................................. H8-225512

[51] Int. Cl.$^6$ ....................................................... A61K 31/41
[52] U.S. Cl. ............................................. 514/360; 514/359
[58] Field of Search ....................................... 514/359, 360

[56] References Cited

U.S. PATENT DOCUMENTS

| | | | |
|---|---|---|---|
| 4,757,063 | 7/1988 | Parnham | 514/359 |
| 5,246,951 | 9/1993 | Galet et al. | 514/359 |

FOREIGN PATENT DOCUMENTS

WO 92/02221  2/1992  WIPO .

OTHER PUBLICATIONS

"The neuroprotective efficacy of ebselen (a glutathione peroxidase mimic) on brain damage induced by transient focal cerebral ischaemia in the rat," Dawson et al., *Neuroscience Letters*, 185 (1995) pp. 65–69.

"Ebselen (PZ–51) Protects the Caudate Putamen Against Hypoxia/Ischemia Induced Neuronal Damage," Knollema et al., *Neuroscience Research Communications*, vol. 19, No. 1, Jul.–Aug. 1996, pp. 47–56.

"The Role of Free Radicals in Toxicity and Disease," Sidney J. Stohs, *Journal of Basic and Clinical Physiology and Pharmacology*, vol. 6, No. 3–4, 1995, pp. 205–228.

*Primary Examiner*—Theodore J. Criares
*Attorney, Agent, or Firm*—Proskauer Rose LLP

[57] ABSTRACT

The present invention is directed to a drug for preventing or remedying Alzheimer's disease. The drug contains as the active ingredient 2-phenyl-1,2-benzisoselenazol-3(2H)-one (referred as compound (A)), whose effect is based on the action of reducing neuron toxicity induced by β-amyloid protein.

17 Claims, No Drawings

PREVENTIVE OR THERAPEUTIC DRUG FOR ALZHEIMER'S DISEASE

FIELD OF THE INVENTION

The present invention relates to a preventive or therapeutic drug for Alzheimer's disease containing as the active ingredient 2-phenyl-1,2-benzisoselenazol-3(2H)-one, whose effect is based on the action of reducing neuron toxicity induced by β-amyloid protein.

BACKGROUND ART

In some countries, acetylcholinesterase inhibitors such as physostigmine or tetrahydroaminoacridine (THA) are used as preventive or therapeutic drugs for Alzheimer's disease. However, successful results have not been obtained. It has also been attempted to develop 5-HT agonists acting on the nerve e system, but their mechanism has not yet been completely elucidated.

Pathological traits of Alzheimer's disease include senile plaques and accumulation of PHFs (paired helical filaments) in the brain.

The β-amyloid protein (hereinafter referred to as Aβ), which is the main component of senile plaques, is an insoluble peptide constituted by approximately 40 amino acid residues. It has been elucidated that Aβ itself damages neurons biochemically, and particularly that coagulated Aβ—not solubilized Aβ—is responsible for this effect.

Thus, it has been desired that a substance useful for preventing the progress of or for curing Alzheimer type senile dementia be discovered and developed as a pharmaceutical based on the mechanism of suppressing death of neurons incurred by toxic Aβ.

SUMMARY OF THE INVENTION

The present inventors conducted extensive studies toward finding low molecular compounds that are capable of passing through the brain blood flow barrier (BBB) and that have an effect of reducing neuron toxicity of Aβ, and found that 2-phenyl-1,2-benzisoselenazol-3(2H)-one (herein after referred to as compound A) has an excellent action, leading to completion of the present invention.

Compound A which is used in the present invention has an effect of inhibiting the death of neurons, which death is caused in the presence of Aβ. Thus, use of compound A as a preventive or therapeutic drug for Alzheimer's disease is expected.

DETAILED DESCRIPTION OF THE INVENTION

Aβ was identified as a main constituent of senile plaques, one of the pathological traits of Alzheimer's disease. It is composed of 39–43 amino acid residues. It is also known that Aβ aggregates and exhibits neurotoxicity to induce cellular death. It has recently been found that death of PC12 cells in the presence of Aβ, attributed to neurotoxic Aβ, is suppressed when compound A (ebselen) is added. Therefore, compound A is expected to be an excellent preventive or therapeutic drug for Alzheimer's disease.

Compound A used in the present invention may be synthesized through a process disclosed in Japanese Patent Publication (kokoku) No. 2-38591 (Japanese Patent Application Laid-Open (kokai) No. 57-67568). Compound A may be produced by reaction of 2-methylseleno-2-phenyl-benzamide with phosphorous pentachloride and subsequent hydrolysis, as described in U.S. Pat. No. 4,757,063 (Parnham) and in R. Weber et al., *Bulletin de la Soc. Chim de France*, 1986 (7/8), pgs. 1124–1126. All of the foregoing references are incorporated herein by reference.

Compound A can be transformed into various forms such as tablets, capsules, powders, granules, syrups, and injections using known formulation techniques together with additives including vehicles, binders, disintegrants, and solubilizers.

The following is an exemplary formulation:

| Tablets: | |
|---|---|
| Compound A | 50 mg |
| Carboxymethylcellulose | 25 mg |
| Starch | 5 mg |
| Crystalline cellulose | 40 mg |
| Magnesium stearate | 2 mg |
| Total | 122 mg |

Compound A exerts its primary expected effect in any manner of administration, e.g., ordinary oral administration or peroral administration such as injection.

In the case of oral administration, the dose of compound A is between 100 and 2,000 mg/day for an adult, and preferably between 200 and 1,000 mg/day, which may be suitably increased or decreased depending on the clinical condition of the patient.

Toxicity of compound A has been studied by obtaining $LD_{50}$ values in mice and rats. According to the inventors' experiments, the $LD_{50}$ values obtained on mice were $\geq 6,810$ mg/kg in the case of oral administration, and 740 mg/kg in the case of intraperitoneal administration. Similarly, the $LD_{50}$ values obtained on rats were $\geq 6,810$ mg/kg in the case of oral administration, and 580 mg/kg in the case of intraperitoneal administration. Thus, these $LD_{50}$ values prove that compound A is a very safe compound.

Moreover, even when a high dose of compound A was administered to mice or rats, no problematic adverse side effects were observed.

The present invention will next be described by way of example, which should not be construed as limiting the invention.

EXAMPLE 1

Effect of compound A to inhibit neuron death in the presence of Aβ:

PC12 cells (derived from rats, chromaffin tumor) were cultured and subcultured in a 100 mm dish (made of Corning) coated with polylysine and containing a DMEM medium supplemented with 10% FCS and 5% horse serum (product of Sigma). Briefly, PC12 cells ($1 \times 10^6$ cells/dish) were seeded in a 100 mm dish coated with polylysine. In order to induce differentiation of the PC12 cells, the cells were grown for 7 days in a DMEM medium containing 5% FCS, 50 ng/ml NGF, and 1% horse serum. The PC12 cells were then peeled off through pipetting and suspended in a suitable medium to prepare a cell suspension. The cell suspension was seeded into each well of a polylysine-coated 96-well dish ($1 \times 10^4$ cells/well). Subsequently, Aβ (Bachem Feinchmikalien AG) was added so that a final concentration of 10 μM was achieved. Compound A was also added so that a final concentration of 0.1, 1.0, or 2.5 μM was achieved. As controls, compound B (compound A substituted by sulfur; having no glutathione peroxidase-like activities; 2-phenyl- 1,2-benzothiazol-3(2H)-one; provided by Nattermann) was added at the same concentrations in a similar manner. The cells were cultured for 48 hours from the addition of compound A or compound B.

An MTT reagent (3-(4,5-dimethylthiazole-2-yl)-2,5-diphenyl tetrazolium bromide) was added to the thus-treated cells, incubation was performed for 4 hours, and the cells were lysed. The subsequent procedure was performed using a so-called MTT method, which employs colorimetry based on a reduction reaction of the reagent, to thereby obtain the viability of the cells in the suspension (Behl, C. et al., Cell, 77: 817–827, 1994).

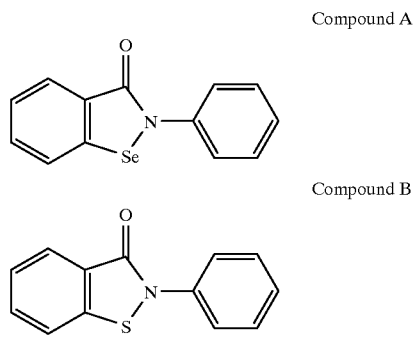

Compound A

Compound B

TABLE 1

Effect of compounds A and B on cellular death of PC12 neurons

| Substances added ($\mu M$) | | | Viability | |
|---|---|---|---|---|
| A$\beta$ | Compound A | Compound B | of cells (% of control) | Student's T-test |
| 1h. 10 | | | | |
| 10 | — | — | 15 ± 9.5 | — |
| 10 | 0.1 | — | 45 ± 2.1 | * |
| 10 | — | 0.1 | 14 ± 4.5 | |
| 10 | 1.0 | — | 59 ± 14.5 | ** |
| 10 | — | 1.0 | 13 ± 1.0 | |
| 10 | 2.5 | — | 66 ± 4.5 | *** |
| 10 | — | 2.5 | 10 ± 5.0 | |

*: $P \leq 0.01$, : $P \leq 0.002$, *: $P \leq 0.0001$, n = 6
The T-test was performed on the groups to which A$\beta$ (10 $\mu M$) was added.

As is apparent from Table 1, death of neurons was caused by A$\beta$, and the death rate could not be suppressed by the addition of compound B. However, when compound A was added in the amount of 0.1 $\mu M$, 1 $\mu M$, or 2.5 $\mu M$, neuron death suppressed significantly in all cases ($P \leq 0.0082$; $P \leq 0.0018$; and $P \leq 0.0001$).

EXAMPLE 2

PC12 cells (derived from rats, chromaffin tumor) were cultured and subcultured in a 100 mm dish (made of Corning) coated with polylysine and containing a DMEM medium supplemented with 10% FCS and 5% horse serum (product of Sigma). Briefly, PC12 cells ($1 \times 10^6$ cells/dish) were seeded in a 100 mm dish coated with polylysine. In order to induce differentiation of the PC12 cells, the cells were grown for 7 days in a DMEM medium containing 5% FCS, 50 ng/ml NGF, and 1% horse serum. The PC12 cells were then peeled off through pipetting and suspended in a suitable medium to prepare a cell suspension. The cell suspension was seeded into each well of a 60 mm, polylysine-coated 96-well dish ($1 \times 10^4$ cells/well). After adhesion of the cells was confirmed, the following procedure was performed.

The thus-adhered PC12 cells were placed in a DMEM medium. To the cells were added 10 $\mu M$ of SNAP and 2.5 $\mu M$ of compound A. For control groups, only SNAP was added. Each sample was incubated for 3 hours. Thereafter, a solution of DCFH-DA (Molecular Probes, Inc.) in DMSO (1 mg/413 $\mu l$) which had been prepared in advance was added to each PC12-containing sample so that a final concentration of 5 $\mu M$ was obtained, and the samples were then incubated for 30 minutes. The cells were removed using trypsin-EDTA, and recovered via centrifugation (1,000 rpm×5 min.). The recovered cells were suspended in 50 $\mu l$ of PBS(-) while being cooled with ice. The amount of intracellular hydrogen peroxide was determined using a flow cytometer; The cell suspension was subjected to FACS (fluorescence-activated cell sorting), and the amount of the fluorescent substance, 2',7'-dichlorofluorescin (DCFH), which had been oxidized by peroxides was measured. As a result, in the case where SNAP was added, it was found that generation of hydrogen peroxide increased to the level of 1.3–1.4 times higher than the level achieved in the case where SNAP was not added. Moreover, the increased hydrogen peroxide generation attributed to the addition of SNAP was significantly suppressed by the addition of 2.5 $\mu M$ of compound A ($P \leq 0.0015$).

TABLE 2

Effect of compound A on suppressing generation of hydrogen peroxide induced by NO (in PC12 cells to which SNAP was added)

| Treated with | | Amounts of generated $H_2O_2$ |
|---|---|---|
| SNAP ($\mu M$) | Compound A ($\mu M$) | (% log fluorescence of control) (*) |
| 0 | 0 | 100.0 |
| 10 | 0 | 135.8 ± 5.25 |
| 10 | 2.5 | 45.7 ± 6.03 (**) |

SNAP: S-nitroso-N-acetyl-DL-penicillamine
**: $P \leq 0.0015$ [in accordance with Student's T-test with respect to SNAP (10 $\mu M$); n = 3]

It is considered that NO that is derived from A$\beta$ in turn accelerates generation of hydrogen peroxide. However, as is apparent from Table 2, generation of hydrogen peroxide was satisfactorily suppressed by the addition of 2.5 $\mu M$ of compound A.

Recently, it has been pointed out that apotosis may be related to the death of neurons in Alzheimer's disease. Also, there has been reported that death of neurons is triggered by A$\beta$, and the neurotoxicity is caused by the generation of hydrogen peroxide (Proc. Natl. Acad. Sci. USA., 90: 7951–7955, 1993).

As described above, the addition of compound A significantly suppresses generation of hydrogen peroxide induced by A$\beta$. Therefore, it has been demonstrated that compound A is expected to provide excellent preventive or therapeutic effects on Alzheimer's disease.

Thus, compound A which is used in the present invention is specifically useful as a preventive or therapeutic drug for senile dementia, in particular, Alzheimer's disease.
The abbreviation, used in the description before, means:
Polylysine is a Lysine-Polypeptide with a variable chain length;
DMEM means Delbecco's modified Eagle's medium;
DCFH is 2',7'-dichlorofluorescin;
FCS means fetal calf serum;

DMSO is dimethyl sulphoxide;
Trypsin EDTA is a complexing agent on the basis of ethylendiamine tetraacetic acid and
NO is nitrogen oxide.

We claim:

1. A method for treating a disease characterized by an elevated level of β-amyloid protein in a mammal, comprising administering to said mammal a therapeutically effective amount of 2-phenyl-1,2-benzisoselenazol-3(2H)-one.

2. The method of claim 1 wherein said 2-phenyl-1,2-benzisoselenazol-3(2H)-one is administered as the active ingredient of a drug composition.

3. The method of claim 2 wherein said drug composition is administered orally.

4. The method of claim 2 wherein said drug composition is administered perorally.

5. The method of claim 2 wherein said drug composition is administered by injection.

6. A method for treating neuron death in a mammal, comprising administering to said mammal a therapeutically effective amount of 2-phenyl-1,2-benzisoselenazol-3(2H)-one.

7. The method of claim 6 wherein said 2-phenyl-1,2-benzisoselenazol-3(2H)-one is administered as the active ingredient of a drug composition.

8. The method of claim 7 wherein said drug composition is administered orally.

9. The method of claim 7 wherein said drug composition is administered perorally.

10. The method of claim 7 wherein said drug composition is administered by injection.

11. A method for treating Alzheimer's disease, comprising orally administering a composition containing a therapeutically effective amount of 2-phenyl-1,2-benzisoselenazol-3(2H)-one as an active ingredient.

12. The method of claim 11 wherein the composition is a preparation selected from the group consisting of tablets, capsules, powders, granules and syrups.

13. The method of claim 11 wherein the composition is administered in an adult dosage containing a daily amount of 2-phenyl-1,2-benzisoselenazol-3(2H)-one in a range of about 100 mg to about 2,000 mg.

14. The method of claim 11 wherein the composition is administered in an adult dosage containing a daily amount of 2-phenyl-1,2-benzisoselenazol-3(2H)-one in a range of about 200 mg to about 1,000 mg.

15. A method for treating Alzheimer's disease, comprising perorally administering an injectable composition containing a therapeutically effective amount of 2-phenyl-1,2-benzisoselenazol-3(2H)-one as an active ingredient.

16. The method of claim 15 wherein the composition is administered in an adult dosage containing a daily amount of 2-phenyl-1,2-benzisoselenazol-3(2H)-one in a range of about 100 mg to about 2,000 mg.

17. The method of claim 15 wherein the composition is administered in an adult dosage containing a daily amount of 2-phenyl-1,2-benzisoselenazol-3(2H)-one in a range of about 200 mg to about 1,000 mg.

* * * * *